United States Patent [19]

Kresge et al.

[11] Patent Number: 4,599,475
[45] Date of Patent: Jul. 8, 1986

[54] PROCESS FOR XYLENE ISOMERIZATION USING ZSM-23 ZEOLITE

[75] Inventors: Charles T. Kresge, Ellicott City, Md.; James C. Vartuli, West Chester, Pa.; Michael P. Nicoletti, Turnersville, N.J.

[73] Assignee: Mobil Oil Corporation, New York, N.Y.

[21] Appl. No.: 747,736

[22] Filed: Jun. 19, 1985

Related U.S. Application Data

[63] Continuation-in-part of Ser. No. 662,750, Oct. 19, 1984, abandoned, which is a continuation-in-part of Ser. No. 536,471, Sep. 28, 1983, abandoned.

[51] Int. Cl.$^4$ ............................................. C07C 5/22
[52] U.S. Cl. ..................................... 585/481; 502/71; 502/77
[58] Field of Search ................... 502/71, 77; 585/477, 585/481, 482

[56] References Cited

U.S. PATENT DOCUMENTS

| | | | |
|---|---|---|---|
| 3,130,007 | 4/1964 | Breck | 423/328 |
| 4,076,842 | 2/1978 | Plank et al. | 423/328 |
| 4,151,189 | 4/1979 | Rubin et al. | 423/329 |
| 4,181,811 | 1/1980 | Young | 585/486 |
| 4,255,600 | 3/1981 | Young | 585/362 |
| 4,309,281 | 1/1982 | Dessau | 585/820 |
| 4,326,994 | 4/1982 | Haag et al. | 502/77 |
| 4,372,930 | 2/1983 | Short et al. | 423/326 |
| 4,385,195 | 5/1983 | Butter et al. | 585/481 |
| 4,397,825 | 8/1983 | Whittam | 502/65 |
| 4,547,605 | 10/1985 | Kresge et al. | 585/467 |

FOREIGN PATENT DOCUMENTS

| | | | |
|---|---|---|---|
| 42225 | 6/1980 | European Pat. Off. | 502/77 |
| 1567948 | 7/1976 | United Kingdom | 502/77 |

*Primary Examiner*—Andrew H. Metz
*Assistant Examiner*—A. Pal
*Attorney, Agent, or Firm*—A. J. McKillop; M. G. Gilman; L. P. Hobbes

[57] ABSTRACT

An improved process is disclosed for the isomerization of xylenes over a zeolite which may contain a platinum group metal. The improvement resides in the use of ZSM-23 zeolite which exhibits enhanced selectivity which inhibits the production of undesired $C_9^+$ aromatic transalkylation by-products. ZSM-23 having pores substantially unobstructed by silica, such as that made from a forming mixture containing amorphous precipitated silica as a silica source, has been found to be particularly useful in the process of the present invention.

14 Claims, No Drawings

PROCESS FOR XYLENE ISOMERIZATION USING ZSM-23 ZEOLITE

CROSS REFERENCE TO RELATED APPLICATIONS

This case is a continuation in part application of U.S. Ser. No. 662,750, filed Oct. 19, 1984 which is a continuation-in-part of U.S. application Ser. No. 536,471, filed Sept. 28, 1983, now both abandoned, all of which are incorporated herein by reference.

Since the announcement of the first commercial installation of Octafining in Japan in June, 1958, this process has been widely installed for the supply of p-xylene. See "Advances in Petroleum Chemistry and Refining" volume 4, page 433 (Interscience Publishers, New York 1961). The demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point °F. | Boiling Point °F. |
|---|---|---|
| Ethylbenzene | −139.0 | 277.1 |
| P-xylene | 55.9 | 281.0 |
| M-xylene | −54.2 | 282.4 |
| O-xylene | −13.3 | 292.0 |

Principal sources are catalytically reformed naphthas and pyrolysis distillates. The $C_8$ aromatic fractions from these sources vary quite widely in composition but will usually be in the range 2 to 32 wt % ethylbenzene with the balance, xylenes, being divided approximately 50–65 wt % meta, and the balance para and ortho.

Individual isomer products may be separated from the naturally occurring mixtures by appropriate physical methods. Ethylbenzene may be separated by fractional distillation although this is a costly operation. Ortho-xylene may be selected by fractional distillation and is so produced commercially. Para-xylene is separated from the mixed isomers by fractional crystallization or by selective adsorption.

As commercial use of para and ortho-xylene has increased there has been interest in isomerizing the other $C_8$ aromatics toward an equilibrium mix and thus increasing yields of the desired xylenes. At present, several xylene isomerization processes are available and in commercial use.

The isomerization process operates in conjunction with the product xylene or xylenes separation process. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

It will be apparent that separation techniques for recovery of one or more xylene isomers will not have material effect on the ethylbenzene introduced with charge to the recovery/isomerization "loop". That compound, normally present in eight carbon atom aromatic fractions, will accumulate in the loop unless excluded from the charge or converted by some reaction in the loop to products which are separable from xylenes by means tolerable in the loop. Ethylbenzene can be separated from the xylenes of boiling point near that of ethylbenzene by extremely expensive "superfractionation". This capital and operating expense cannot be tolerated in the loop where the high recycle rate would require an extremely large distillation unit for the purpose.

Other isomerization processes operate at higher pressure and temperature, usually under hydrogen pressure in the presence of catalysts which convert ethylbenzene to products readily separated by relatively simple distillation in the loop, which distillation is needed in any event to separate by-products of xylene isomerization from the recycle stream. For example, the Octafining catalyst of platinum on a silica-alumina composite exhibits the dual functions of hydrogenation/dehydrogenation and isomerization.

In Octafining, ethylbenzene reacts through ethyl cyclohexane to dimethyl cyclohexanes which in turn equilibrate to xylenes. Competing reactions are disproportionation of ethylbenzene to benzene and diethylbenzene, hydrocracking of ethylbenzene to ethylene and benzene and hydrocracking of the alkyl cyclohexanes.

The rate of ethylbenzene approach to equilibrium concentration in a $C_8$ aromatic mixture is related to effective contact time. Hydrogen partial pressure has a very significant effect on ethylbenzene approach to equilibrium. Temperature change within the range of Octafining conditions 443° C. to 482° C. (830° F. to 900° F.) has but a very small effect on ethylbenzene approach to equilibrium.

Concurrent loss of ethylbenzene to other molecular weight products relates to percent approach to equilibrium. Products formed from ethylbenzene include $C_6+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than the reaction of ethylbenzene, but they do exhibit different rates of isomerization and hence, with different feed composition situations the rates of approach to equilibrium vary considerably.

Ethylbenzene has been found responsible for a relatively rapid decline in catalyst activity and this effect is proportional to its concentration in a $C_8$ aromatic feed mixture. It has been possible then to relate catalyst stability (or loss in activity) to feed composition (ethylbenzene content and hydrogen recycle ratio) so that for any $C_8$ aromatic feed, desired xylene products can be made with a selected suitably long catalyst use cycle.

A different approach to conversion of ethylbenzene is described in Morrison U.S. Pat. No. 3,856,872, dated Dec. 24, 1974. Over an active acid catalyst typified by zeolite ZSM-5, ethylbenzene disproportionates to benzene and diethylbenzene which are readily separated from xylenes by the distillation equipment needed in the loop to remove by-products. It is recognized that rate of disproportionation of ethylbenzene is related to the rate of conversion of xylenes to other compounds, e.g. by disproportionation. See also Burress U.S Pat. No. 3,856,873 which also describes reaction of $C_8$ aromatics over ZSM-5 and shows effects of various temperatures up to 950° F. in the absence of metal co-catalyst and in the absence of hydrogen In the known processes for accepting ethylbenzene to the loop, conversion of that compound is constrained by the need to hold conversion of xylenes to other compounds to an acceptable level. Thus, although the Morrison technique provides significant advantages over Octafining in this respect, operating conditions are still selected to balance the advantages of ethylbenzene conversion against the disadvantages of xylene loss by disproportionation and the like.

U.S. Pat. No. 4,163,028 discloses zeolite isomerization and ethylbenzene conversion at high temperatures with ZSM-5 of very high silica to alumina ratio whereby the acid activity is reduced. U.S. Pat. No. 4,236,996 to Tabak and Morrison discloses xylene isomerization concurrently with ethylbenzene conversion utilizing a certain steamed ZSM-5 catalyst. Conversion temperature of 700° F. to 1000° F. is described, the preferred conversion temperature being 800° F. or higher. An improved method for preparation of platinum supported on ZSM-5 of controlled acidity is disclosed in U.S. Pat. No. 4,312,790 to Butter and Chester, the entire content of which is incorporated herein by reference.

The entire contents of U.S. Pat. Nos. 3,856,872; 3,856,873; 4,163,028, 4,236,996; and 4,312,790 are incorporated herein by reference.

The above recited art notwithstanding, there remain certain problems in the conversion of $C_8$ aromatics fractions which contain ethylbenzene. By their very nature, all of the proposed processes involve the high temperature isomerization of xylenes followed by reduction of temperature to crystallize paraxylene from the unwanted isomers, reheating of the recycle stream to high temperature, and repetition of this cycle to exhaustively convert xylenes to para-xylene. Thus, the processes occur at temperatures which are conducive to transalkylation reactions and the formation of transalkylation intermediates which ultimately results in xylene loss. In the past, efforts have been made to prevent the formation of the relatively bulky $C_9^+$ transalkylation intermediates and the resulting xylene loss by reducing the effective pore size of the ZSM-5 zeolite. U.S. Pat. No. 3,906,054 discloses a method for reducing the effective pore size of ZSM-5 zeolite by incorporating a small amount of phosphorous with the crystal structure. However, such catalysts may suffer from diffusion of the phosphorus from the crystal structure, particularly if water is present in the feed.

It has now been found that formation of $C_9^+$ residue products from transalkylation reactions can be inhibited in xylene isomerizations even at temperatures greater than about 315° C. (600° F.) by employing ZSM-23 catalyst which has a slightly smaller pore diameter than ZSM-5 (4.5×5.6 A versus 4.8×7.1 A). Because of the reduced pore size of ZSM-23 relative to ZSM-5, the formation of transalkylation intermediates of undesired $C_9^+$ aromatics is reduced. This results in a significant increase in ethylbenzene selectivity. It has also been found that the catalyst activity of ZSM-23 employed in the alkylation ot aromatics is significantly increased where ZSM-23 is made from a forming mixture which contains an amorphous precipitated silica.

The present invention particularly relates to a process for isomerizing an isomerization feed containing an aromatic $C_8$ mixture of ethylbenzene and xylene by which process the para-xylene content is enhanced. The feed is contacted under conversion conditions with a catalyst comprising a trans-alkylation inhibiting ZSM-23 zeolite having a silica to alumina ratio of at least about 12 and a constraint index within the approximate range of 1 to 12. Preferably, the ZSM-23 material is a catalyst whose pores are substantially unobstructed by silica. In a particularly preferred embodiment the ZSM-23 zeolite is prepared from a forming mixture containing amorphous precipitated silica as a silica source.

The present invention further contemplates the use of ZSM-23 in the acid form (HZSM-23) or ZSM-23 which contains a Group VIII or platinum group metal, such as platinum.

The xylene isomerization processing conditions of the present invention may include a hydrogen to hydrocarbon ratio in the range of 0.1 to 10, and preferably 1 to 5, a temperature of from about 260° C. (500° F.) to about 538° C. (1000° F.), preferably in excess of 343° C. (650° F.), a pressure of about 0 to about 1500 psig and a weight hourly space velocity of between about 0.5 and about 100.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of small cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline materials such as aluminosilicates. These materials can be described as a rigid three-dimensional framework of $XO_4$ and $YO_4$ wherein X is silicon and/or germanium, and Y is one or more of aluminum, gallium, iron, chromium, vanadium, molybdenum, arsenic, manganese, or boron. This framework is comprised of tetrahedra which are cross-linked by the sharing of oxygen atoms whereby the ratio of the total Y and X atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of Y to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given zeolite by suitable selection of the cation. The spaces between the tetrahedra are occupied by molecules of water prior to dehydration.

The crystalline zeolites utilized by the method of the present invention are members of a special class of zeolitic materials which exhibit unusual properties. Although these zeolites have unusually low Y atom contents, i.e. high X to Y mole ratios, e.g., high silica-alumina ratios, they are very active even when the X to Y mole ratio exceeds 30. The activity is surprising, since catalytic activity is generally attributed to framework Y atoms and/or cations associated with these atoms. These zeolites retain their crystallinity for long periods in spite of the presence of steam at high temperatures which induces irreversible collapse of the framework of other zeolites, e.g. of the X and A type. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e., the pore windows of the structure are of about a size such as would be provided by 10-membered rings of silicon atoms interconnected by oxygen atoms.

The catalyst useful in this invention is known as ZSM-23. The ZSM-23 composition has a characteristic X-ray diffraction pattern, the values of which are set out in Table I, below. The ZSM-23 zeolite composition, for the purposes of the present invention, can also be identified, in terms of mole ratios of oxides and in the anhydrous state, as follows:

$$(0.58\text{--}3.4)\, M_{2/n}O:Y_2O_3\text{-}10XO_2$$

wherein M is at least one cation having a valence n, X is silicon and/or germanium, and Y is one or more of aluminum, gallium, iron, chromium, vanadium, molybdenum, arsenic, manganese or boron. A particularly preferred form of ZSM-23 is the aluminosilicate form wherein X is silicon and Y is aluminum.

In a preferred synthesized form, the zeolite has a formula, in terms of mole ratios of oxides and in the anhydrous state, as follows:

$$(0.7\text{--}2.8)R_2O:(0.08\text{--}0.25)M_2O:Y_2O_3:(50\text{--}220)XO_2$$

wherein R is a nitrogen-containing organic cation, such as, for example, that derived from pyrrolidine, M is an alkali metal cation, especially sodium, and X and Y are as described above, particularly where X is silicon and Y is aluminum.

The original cations of the as-synthesized ZSM-23 can be replaced in accordance with techniques well known in the art, at least in part, by ion exchange with other cations. Preferred replacing cations include metal ions, ammonium ions, hydrogen ions and mixtures thereof. Particularly preferred cations are those which render the zeolite catalytically active especially for hydrocarbon conversion. These include hydrogen, rare earth metals, and metals of Groups IIA, IIIB, IVB, VIII, IB, IIB, IIIA, IVA.

The synthetic ZSM-23 zeolite possesses a definite distinguishing crystalline structure whose X-ray diffraction pattern shows substantially the significant lines set forth in Table I.

TABLE I

| d(A) | $I/I_o$ |
|---|---|
| 11.2 ± 0.23 | Medium |
| 10.1 ± 0.20 | Weak |
| 7.87 ± 0.15 | Weak |
| 5.59 ± 0.10 | Weak |
| 5.06 ± 0.10 | Weak |
| 4.50 ± 0.10 | Weak |
| 4.53 ± 0.10 | Strong |
| 3.90 ± 0.08 | Very Strong |
| 3.72 ± 0.08 | Very Strong |
| 3.62 ± 0.07 | Very Strong |

TABLE I-continued

| d(A) | $I/I_o$ |
|---|---|
| 3.54 ± 0.07 | Medium |
| 3.44 ± 0.07 | Strong |
| 3.36 ± 0.07 | Weak |
| 3.16 ± 0.07 | Weak |
| 3.05 ± 0.06 | Weak |
| 2.99 ± 0.06 | Weak |
| 2.85 ± 0.06 | Weak |
| 2.54 ± 0.05 | Medium |
| 2.47 ± 0.05 | Weak |
| 2.40 ± 0.05 | Weak |
| 2.34 ± 0.05 | Weak |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in Angstrom units, corresponding to the recorded lines, were calculated. It should be understood that this X-ray diffraction pattern is characteristic of all the species of ZSM-23 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has previously been subjected to thermal treatment.

Synthetic ZSM-23 zeolites can be used either in the alkali metal containing form, the alkali metal and/or hydrogen form, or univalent or multivalent cationic form. They can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Combinations of the aforenoted metals may also be used. Such components can be exchanged or cocrystallized into the composition, impregnated thereon or physically intimately admixed therewith. Such components can be impregnated in or on to ZSM-23 such as, for example, by, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

As prepared, R can be a cation derived from pyrrolidine present in a quantity not less than 50 percent of the cation content.

M can be one or more or a variety of alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Non-limiting examples of such suitable alkali meal ions include sodium and potassium.

Synthetic ZSM-23, when employed either as an adsorbent or as a catalyst in a hydrocarbon conversion process, should be dehydrated at least partially. This can be done by thermal treatment, i.e. heating, to a temperature in the range of 50° C. to about 900° C. in an inert temperature, such as air, nitrogen, etc. and at atmospheric or subatmospheric pressures for between 1 and 48 hours. Dehydration can also be performed at lower temperature merely by placing the catalyst in a vacuum, but a longer time is required to obtain a sufficient amount of dehydration.

Zeolite ZSM-23 can be conventionally prepared by preparing a solution containing sources of an alkali metal oxide, preferably sodium oxide, sources of nitrogen-containing cation, preferably pyrrolidine, an oxide of Y as described above, an oxide of X as described above, and water having a composition, in terms of mole ratios of oxides, falling within the following ranges:

$R^+/(R^+ + M^+)$: 0.25–0.95, preferably 0.40–0.70
$OH/SiO_2$: 0.01–0.5, preferably 0.03–0.2
$H_2O/OH$: 100–2000, preferably 200–600
$XO_2/Y_2O_3$: 12–1000, preferably 50–250 wherein R is an organic nitrogen-containing cation and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions are set out below:

| Temperature (300–375° F.) | 121–204° C. (250–400° F.) | preferably 149–191° C. |
|---|---|---|
| Time | 10–200 hrs. | preferably 16 to 100 hours |

The digestion of the gel particles is carried out until crystals form. The solid product is separated from the reaction medium, as by cooling the whole to room temperature, filtering and water washing.

The crystalline product is dried, e.g. at 110° C. (230° F.), for from about 8 to 24 hours. Of course, milder conditions may be employed if desired, e.g. room temperature under vacuum.

The composition for the synthesis of synthetic ZSM-23 can be prepared utilizing materials which can supply the appropriate oxide. Such compositions include aluminates, alumina, ammonia, silicates, silica hydrosol, silica gel, silicic acid and hydroxides. It will be understood that each oxide component utilized in the reaction mixture for preparing ZSM-23 can be supplied by one or more essential reactants and they can be mixed together in any order. For example, any oxide can be supplied by an aqueous solution, sodium hydroxide or by an aqueous solution of a suitable silicate; the cation derived from pyrrolidine can be either supplied by pyrrolidine or a salt thereof. The reaction mixture can be prepared either batchwise or continuously. Crystal size and crystallization time of the ZSM-23 composition will vary with the nature of the reaction mixture employed.

Further information relating to ZSM-23 and examples of its conventional preparation from colloidal silica can be found in U.S. Pat. No. 4,076,842 incorporated herein by reference.

For the xylene isomerization of this invention, if desired, the ZSM-23 zeolite catalyst can be employed in combination with a support or binder material such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of crystalline aluminosilicate ZSM-23 of the total composition of catalyst and binder or support may vary widely with the ZSM-23 content ranging from between about 1 to about 99 percent by weight and more usually in the range of about 5 to about 80 percent by weight of the composition.

Conventionally prepared ZSM-23 generally exhibits sufficient selectivity such as to prevent excessive formation of undesired residues by transalkylation. However, such materials may lack the desired activity necessary for xylene isomerization. While not wishing to be bound by theory, it is nevertheless believed that pore obstruction by silica and/or silicon causes the reduced activity of such catalysts. Accordingly, a particularly preferred embodiment of the present invention utilizes a type of ZSM-23 whose pores are substantially unobstructed by silica which exhibits significantly increased activity in xylene isomerization. Such ZSM-23 may be prepared from a forming mixture which contains amorphous precipitated silica as the silica source. Commonly assigned U.S. application Ser. No. 509,671, filed June 30, 1983, now abandoned, and its continuation Ser. No. 689,518, filed Nov. 5, 1984, both of which are incorporated herein by reference, disclose such preparation of zeolites from high solids forming mixtures. The use of such materials as catalysts in aromatic alkylation is disclosed in U.S. application Ser. No. 536,469, filed Sept. 28, 1983 and incorporated herein by reference. ZSM-23 made from forming mixtures containing amorphous precipitated silica as the silica source have been found to be relatively free of silica obstruction in its pores. Accordingly, the activity of the resulting zeolite is greater than one made according to conventional methods wherein the forming mixture is a silica hydrogel. The preferred ZSM-23 zeolite prepared from amorphous precipitated silica exhibits improved sorption properties which make it particularly useful in xylene isomerization. In particular, such zeolites are capable of sorbing greater than about 3.0 weight percent, say about 4.0 or 4.5 weight percent, cyclohexane and greater than about 6.1 weight percent, say about 6.5 or 6.9 weight percent n-hexane when subjected to a partial pressure of about 40 mm of either cyclohexane or n-hexane in a vacuum system at room temperature. The increased n-hexane sorption is believed to result from a decrease in pore occlusion by silica, while the increased cyclohexane sorption may be attributed to an increase in surface area of the zeolite. Indeed, ZSM-23 made from amorphous precipitated silica may have significantly more surface area than conventionally prepared ZSM-23, for example as much as 200 m$^2$/g, 250 m$^2$/g or even greater values.

Preferably, the ZSM-23 employed in the present invention sorbs n-hexane and cyclohexane in a sorption ratio greater than about 1.5 (weight percent n-hexane sorbed/weight percent cyclohexane sorbed). Such sorption ratios can be determined by subjecting the calcined zeolite to a partial pressure of about 40 mm of n-hexane or cyclohexane at room temperature, i.e., 20° to 30° C., say about 25° C., and measuring the uptake when sorption equilibrium is achieved. The sorption ratio may be greater than about 2, for example, the range between about 2 and about 3 or 4.

ZSM-23 which is utilized in this particularly preferred embodiment is prepared from a forming mixture containing sources of silica, alkali metal, and water, wherein precipitated silica is used as a silica source. Upon mixing, a non-gelling forming mixture having a solids content greater than about 5 weight percent is produced, say about 7 to 25 weight percent. The precipitated silica may range in particle size from 0.01 to 100 microns, and may preferably have an average particle size of about 0.02 microns.

The amorphous precipitated silica suitable for producing high activity ZSM-23 can be a synthetic wet-process, hydrated amorphous silica having a particle size range of about 0.01 to 100 microns, containing trace impurities of $Al_2O_3$ and NaCl. Preferably, the particles are of a spherical shape with an average diameter of about 0.02 microns. These particles tend to agglomerate in loose "grape cluster" structures. The precipitated silicas used to form the particularly preferred ZSM-23 used in the present invention generally have an unusually large surface area ranging from about 140 to 160 square meters per gram. Hi-Sil, a product of PPG Industries Chemical Division, FK-320, available from Degussa Corporation, QUSO from PQ Corporation, and ZEOFREE-80 manufactured by J. M. Huber Corporation, have all been found suitable for producing ZSM-23 having significantly reduced silica pore occlusion.

The substitution of amorphous precipitated silica such as Hi-Sil for conventional sources of silica, such as sodium silicate, may be practiced in a wide variety of highly siliceous zeolite syntheses. Generally, ZSM-23 zeolites having a silica to alumina ratio of at least about 12 can be made by preparing a high solids non-gelling forming mixture containing sources of silica, alkali metal, and water wherein amorphous precipitated silica is utilized as the silica source. To increase the yield of the desired zeolite, the solids content of this forming mixture can be greater than about 5 weight percent.

In addition to sources of silica, alkali metal and water, optional ingredients in the forming mixture include surfactants, soluble aluminum compounds such as alum ($Al_2(SO_4)_3$), sodium chloride, as well as ZSM-23 seed crystals.

It is contemplated that any feedstock containing an aromatic $C_8$ mixture comprising ethylbenzene and ortho-, meta-, and para-xylene may be used as feed to the process of this invention. Generally, such mixture will have an ethylbenzene content in the approximate range of 5–50 wt. %, an ortho-xylene content in the approximate range of 0–15 wt. %, and a meta-xylene content in the approximate range of 0–70 wt. 70. The feed may also contain non-aromatic hydrocarbons, i.e., naphthenes and paraffins. In a preferred embodiment, the invention provides means to process a mixture of $C_8$ aromatics to a mixture of reduced ethylbenzene content and increased content of para-xylene. It is contemplated that the present invention is particularly useful in the processing of hydrocarbon xylene feeds which contain high concentrations of ethylbenzene, i.e., greater than about 10 weight percent, e.g., about 30 to 50 weight percent.

In accordance with the present invention, such feed is brought into contact, under conversion conditions, with a catalyst comprising a ZSM-23 zeolite having a silica to alumina ratio of at least about 12 and a constraint index within the approximate range of 1 to 12.

The preferred catalyst will contain from about 0.01% to about 1%, preferably about 0.05% to about 0.10 wt. % by weight of platinum to provide mild hydrogenation activity. The catalyst is prepared by conventional techniques including impregnation, base exchange, drying and air calcination. If desired, the activity of the catalyst can be modified by steaming for 1 or more hours at temperatures upwards of 149° C. (300° F.), the time, pressure and temperature being interrelated such that less time is required at higher temperatures and/or pressures.

In the process of this invention, the feed is contacted with the above-described catalyst at a temperature between about 260° C. (500° F.) to about 510° C. (950° F.); a contact time equivalent to or the same as a weight hourly space velocity (WHSV) of about 0.5 to about 50, preferably about 5 to about 25, and a pressure of about 0 to about 1500, preferably between about 20 and about 400 psig.

The reaction product effluent from the process of the invention contains ethane, benzene, toluene and other aromatic hydrocarbons with high selectivity for para-xylene. The use of the ZSM-23 zeolite, particularly that which is made from amorphous precipitated silica, has been found to reduce the formation of transalkylation $C_9+$ aromatic by-products, such as trimethylbenzene, and ethylxylene.

The following examples will serve to illustrate the process of this invention without limiting the same.

EXAMPLE 1

Preparation of Conventional HZSM-23 Catalyst

A silicate solution was prepared by mixing 52 parts colloidal silica (30% by weight) and 67 parts water. An aluminate solution was prepared by combining 9 parts water, 1 part sodium aluminate, 0.3 parts sodium hydroxide (50% by weight) and 5.5 parts pyrrolidine. These two solutions were combined with stirring in an autoclave. The reactants were mixed at room temperature for one hour. The autoclave was heated to 171° C. (340° F.) and maintained at this temperature for 72 hours. The resultant zeolite was then filtered, washed in a Buchner funnel and dried overnight at 121° C. (250° F.). The x-ray diffraction analysis indicated that the zeolite was ZSM-23 and the chemical analysis indicated that the silica to alumina molar ratio was 64. The zeolite was then calcined in flowing nitrogen at 538° C. (1000° F.) for three hours, slurried with an aqueous ammonium nitrate solution at room temperature for cation exchange, and finally calcined in air at 538° C. (1000° F.). The finished zeolite sample was subjected to a partial pressure (40 mm) of either normal hexane or cyclohexane at room temperature in a vacuum system and the uptake of each gas was recorded as follows:

| Absorption (wt %) | | Ratio of Normal Hexane |
|---|---|---|
| Normal Hexane | Cyclohexane | to Cyclohexane |
| 2.5 | 2.1 | 1.2 |

Surface area was determined to be about 149 $m^2$/g.

EXAMPLE 2

Preparation of HZSM-23 Catalyst from a Forming Mixture Comprising Amorphous Precipitated Silica as a Silica Source A silica solution was prepared by mixing 14 parts HiSil 233 (90% silica by weight) and 54 parts water. An alumina solution was prepared by combining 31 parts water, 1 part aluminum sulfate, 0.9 parts sodium hydroxide (50% by weight) and 4.4 parts pyrrolidine. These two solutions were combined with stirring in an autoclave. The combined solution was mixed at room temperature for one hour. The autoclave was heated to 171° C. (340° F.) and maintained at that temperature for 88 hours. The resultant zeolite was then filtered, washed in a Buchner funnel and dried overnight at 121° C. (250° F.). X-ray diffraction analysis indicated that the zeolite was ZSM-23 and the chemical analysis indicated that the silica to alumina molar ratio was 72. The zeolite was then calcined in flowing nitrogen at 538° C. (1000° F.) for three hours, slurried with an aqueous ammonium nitrate solution at room temperature for cation exchange, and finally calcined in air at 538° C. (1000° F.). The finished zeolite sample was subjected to a partial pressure (40 mm) of either normal hexane or cyclohexane at room temperature in a vacuum system and the uptake of each gas was recorded as follows:

| Absorption (wt %) | | Ratio of Normal Hexane to Cyclohexane |
|---|---|---|
| Normal Hexane | Cyclohexane | |
| 6.9 | 4.5 | 1.5 |

Surface area was determined to be about 276 m²/g.

EXAMPLE 3

Preparation of Platinum-Containing HZSM-23 Extrudate

A 65/35 HZSM-23/Al$_2$O$_3$ catalyst extrudate was prepared in the following manner. The zeolite from Example 2 was mixed with gamma alumina to make a mixture of 65 parts zeolite and 35 parts alumina (by weight). Enough water was added to the mixture so that the resulting catalyst could be formed into 1/16" extrudates. These extrudates were activated by first calcining in nitrogen at 540° C. (1000° F.) followed by aqueous exchanges with ammonium nitrate solution and finally calcining in air at 540° C. (1000° F.).

5 g of the activated extruded catalyst were placed in a beaker. While the beaker was agitated, 2.95 ml of an aqueous solution of [Pt(NH$_3$)$_4$]Cl$_2$ containing the equivalent of 0.1 wt % Pt was added to the extrudate. The volume of Pt solution was determined by incipient wetness techniques. The Pt-containing HZSM-23 extrudates were allowed to stand at ambient temperature for 6 hours and were then dried for 18 hours in a forced air draft at over 121° C. (250° F.). The dried extrudates were then calcined for one hour at 538° C. (1000° F.) in air.

EXAMPLE 4

Aromatics Screening Test Comparing Transalkylation Promoting Tendencies of Conventionally Prepared ZSM-23 and ZSM-23 Prepared from a Forming Mixture Containing Amorphous Precipitated Silica The catalytic results presented in Table 1 were obtained from an aromatics screening test which follows the conversion of ethylbenzene and m-xylene. The formation of diethylbenzene and trimethylbenzene isomers from ethylbenzene and m-xylene, respectively, serves as an accurate indicator of the transalkylation promoting tendencies of the catalyst under investigation. The greater this tendency for transalkylation the higher the potential for xylene losses. The test conditions were as follows:

1.0 g catalyst
H$_2$ reduction at 399° C. (750° F.)
Charge Stock: ethylbenzene or m-xylene
Temperature: 399° C. (750° F.)
WHSV: 10 hr$^{-1}$
H$_2$/HC: 3
Pressure: 0 psig Table 1 compares the screening test results obtained for the conventionally prepared ZSM-23 catalyst of Example 1 vs a ZSM-23 based catalyst prepared as described in Example 2. Both catalysts were in the acid form and did not contain platinum group metals. The test results indicate that the ZSM-23 prepared according to the present invention has a significantly greater activity for the conversion of both ethylbenzene and m-xylene than the conventionally prepared ZSM-23.

TABLE 1

| ZSM-23 Activity Comparison | | |
|---|---|---|
| | Conventional ZSM-23 of Ex. 1 | Improved ZSM-23 of Ex. 2 |
| Zeolite: SiO$_2$/Al$_2$O$_3$ | 64 | 70 |
| Extrudate: Zeolite/Binder | 65/35 | 65/35 |
| Ethylbenzene Conversion (Wt %) | 4.81 | 9.57 |
| M-Xylene Conversion (Wt %) | 24.19 | 37.66 |

EXAMPLE 5

Aromatics Screening Test Comparing Transalkylation Promoting Tendencies of HZSM-5 Platinum-Containing Catalysts with HZSM-23 Platinum-Containing Catalyst of Example 3

A 0.1 wt % platinum-containing HZSM-5 catalyst prepared in accordance with Example 5 of U.S. Pat. No. 4,312,790 was compared with the platinum-containing HZSM-23 catalyst of Example 3 in a screening test under the same conditions given in Example 4. The results of this comparison are given in Table 2. The screening test results indicate that under the same operating conditions, the ZSM-23 catalyst possesses a superior ability to convert both m-xylene and ethylbenzene with a reduced selectivity towards transalkylation and thus lower xylene losses.

TABLE 2

| Transalkylation Activity Comparison | | |
|---|---|---|
| Catalyst | ZSM-5 | ZSM-23 of Ex. III |
| Ethylbenzene Conv., Wt % | 5.69** | 10.11 |
| Diethylbenzene, Wt % | | |
| Yield | 1.48 | 0.24 |
| Selectivity* | 26.01 | 2.37 |
| M-Xylene Conv., Wt % | 32.91 | 36.53 |

TABLE 2-continued

| Transalkylation Activity Comparison | | |
|---|---|---|
| Catalyst | ZSM-5 | ZSM-23 of Ex. III |
| Trimethylbenzene, Wt % | | |
| Yield | 0.38 | 0.11 |
| Selectivity | 1.15 | 0.30 |

*Selectivity = $\frac{\text{wt \% yield}}{\text{total conversion}} \times 100$

**Conversion data corrected for 65/35 zeolite/binder

What is claimed is:

1. A process for isomerizing an isomerization feed containing an aromatic $C_8$ mixture of ethylbenzene and xylene by which ethylbenzene and m-xylene conversion is enhanced, said process comprising contacting said feed under conversion conditions with a catalyst comprising ZSM-23 zeolite having a silica to alumina ratio of at least about 12, which zeolite is capable of sorbing greater than about 3 weight percent cyclohexane and greater than about 6.1 weight percent n-hexane.

2. A process for isomerizing an isomerization feed containing an aromatic $C_8$ mixture of ethylbenzene and xylene by which ethylbenzene and m-xylene conversion is enhanced, said process comprising contacting said feed, under conversion conditions with a catalyst comprising ZSM-23 zeolite having a silica to alumina ratio of at least about 12, capable of sorbing greater than about 3 weight percent cyclohexane and greater than about 6.1 weight percent n-hexane, which zeolite is prepared from a forming mixture containing amorphous precipitated silica as a silica source.

3. The process of claim 2 wherein said zeolite contains a Group VIII metal.

4. The process of claim 3 wherein said Group VIII metal is platinum.

5. The process of claim 2 wherein said zeolite is capable of sorbing greater than about 3.5 weight percent cyclohexane and 6.5 weight percent n-hexane.

6. The process of claim 2 wherein said conversion conditions include a temperature of from about 260° C. to about 538° C., a pressure of about 0 to about 1500 psig and a weight hourly space velocity of between about 0.5 and about 100.

7. The process of claim 2 wherein said aromatic $C_8$ mixture contains ethylbenzene, para-xylene, meta-xylene, and ortho-xylene.

8. The process of claim 2 wherein said zeolite is ZSM-23 predominately in the hydrogen form.

9. The process of claim 1 wherein said zeolite can sorb n-hexane and cyclohexane at a sorption ratio greater than about 1.5 weight percent n-hexane sorbed/weight percent cyclohexane sorbed at 40 mm partial pressure and room temperature.

10. The process of claim 9 wherein said sorption ratio is greater than about 2.

11. The process of claim 9 wherein said sorption ratio ranges between about 2 and about 4.

12. The process of claim 2 wherein said zeolite can sorb n-hexane and cyclohexane in a sorption ratio greater than about 1.5 weight percent n-hexane sorbed/weight percent cyclohexane sorbed at 40 mm partial pressure and room temperature.

13. The process of claim 12 wherein said sorption ratio is greater than about 2.

14. The process of claim 12 wherein said sorption ratio ranges between about 2 and about 4.

* * * * *

UNITED STATES PATENT AND TRADEMARK OFFICE
CERTIFICATE OF CORRECTION

PATENT NO. : 4,599,475
DATED : July 8, 1986
INVENTOR(S) : C. T. Kresge, J. C. Vartuli, M. P. Nicoletti It is certified that error appears in the above-identified patent and that said Letters Patent is hereby corrected as shown below:

Column 5, line 25, the formula "$(0.58-3.4)M_{2/n}O:Y_2O_2-10XO_2$" should read:

-- $(0.58-3.4)M_{2/n}O:Y_2O_3-10XO_2$ --

Signed and Sealed this

Eighteenth Day of November, 1986

Attest:

DONALD J. QUIGG

Attesting Officer

Commissioner of Patents and Trademarks